(12) United States Patent
Sagel et al.

(10) Patent No.: US 6,461,158 B1
(45) Date of Patent: Oct. 8, 2002

(54) PRODUCTS AND METHODS THAT SIMULATE CHANGES IN TOOTH COLOR

(75) Inventors: Paul Albert Sagel, Mason, OH (US); Philippe G. Lapujade, Framingham, MA (US); Melissa Ellen Jeffers, Wyoming, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 0 days.

(21) Appl. No.: 09/638,822

(22) Filed: Aug. 14, 2000

(51) Int. Cl.[7] ............................. A61B 1/24; A61C 5/00
(52) U.S. Cl. .................... 433/30; 433/215; 359/884
(58) Field of Search ................ 433/30, 31, 215; 359/884

(56) References Cited

U.S. PATENT DOCUMENTS

| | | | |
|---|---|---|---|
| 1,979,119 A | 10/1934 | Radzinsky | 434/100 |
| 2,560,724 A * | 7/1951 | Harrison | 359/884 |
| 3,047,966 A | 8/1962 | Greenspan | 434/371 |
| 3,256,014 A | 6/1966 | Kelsey | 40/442 |
| 3,659,928 A | 5/1972 | Macfarlane | 359/629 |
| 3,711,182 A * | 1/1973 | Jasgur | 359/884 |
| 3,729,839 A | 5/1973 | Bourdier | 434/371 |
| 3,859,987 A | 1/1975 | Holstad | 600/247 |
| 4,084,700 A * | 4/1978 | Dunchock | 211/41 |
| 4,232,334 A | 11/1980 | Dyson | 348/77 |
| 4,273,418 A | 6/1981 | Gillespie et al. | 359/235 |
| 4,592,726 A * | 6/1986 | Brilliant | 433/31 |
| 4,640,685 A | 2/1987 | Croll | 433/141 |
| 4,900,253 A | 2/1990 | Landis | 433/30 |
| 5,288,231 A | 2/1994 | Kuehn et al. | 433/29 |
| 5,509,800 A | 4/1996 | Cunningham et al. | 433/29 |
| 5,648,064 A * | 7/1997 | Gaffar et al. | 424/53 |
| 5,788,579 A | 8/1998 | Cherry et al. | 472/63 |
| 5,860,809 A | 1/1999 | Meehan | 434/100 |
| 5,879,691 A | 3/1999 | Sagel et al. | 424/401 |
| 5,891,453 A | 4/1999 | Sagel et al. | 424/401 |
| 5,894,017 A | 4/1999 | Sagel et al. | 424/401 |
| 5,989,569 A | 11/1999 | Dirksing et al. | 424/401 |
| 6,030,222 A * | 2/2000 | Tarver | 433/215 |
| 6,045,811 A | 4/2000 | Dirksing et al. | 424/401 |
| 6,096,328 A | 8/2000 | Sagel et al. | 424/401 |
| 6,136,297 A | 10/2000 | Sagel et al. | 424/49 |
| 6,277,458 B1 | 8/2001 | Dirksing et al. | 428/42.3 |

* cited by examiner

Primary Examiner—John J. Wilson
(74) Attorney, Agent, or Firm—James C. Vago (57) ABSTRACT

A reflective device is provided. The reflective device includes a reflective layer and a first region which reflects light to form an image that simulates a change in tooth color of at least a portion of a viewer's tooth.

39 Claims, 9 Drawing Sheets

PRODUCTS AND METHODS THAT SIMULATE CHANGES IN TOOTH COLOR

TECHNICAL FIELD OF THE INVENTION

The present invention relates to products that simulate changes in tooth color, and more particularly, the present invention relates to reflective devices comprising a mirror having a region that changes one or more spectral characteristics of light incident thereto to form an image that simulates a viewer's teeth before, during and/or after whitening.

BACKGROUND OF THE INVENTION

Currently, there are many tooth-whitening programs available in the marketplace, such as toothpastes containing whiteners, tooth-whitening systems administered by dentists during office visits, and home kits provided by both dentists and non-professionals that are available at drug stores. Although tooth whitening has been growing in popularity, many consumers do not use or take full advantage of the products that are available. For example, some consumers fail to recognize the extent to which stained or yellowed teeth can adversely affect one's appearance and whitened teeth and a bright smile can dramatically improve one's appearance. Other consumers who begin a whitening program often quit before the whitening process has been completed. Many tooth-whitening programs require time-consuming regimens. Consumers that do not see immediate results may become discouraged and not complete the regimen. Also, once teeth are whitened, they inevitably slowly lose their whiteness and brightness over time at a gradual rate, with day-to-day changes in whiteness being small. Therefore, with day-to-day changes being small, the consumer may not realize when it is advantageous to reapply the tooth-whitening regimen.

It is known in the art to provide illustrations demonstrating changes in color to teeth. For example, a tooth-whitening system may include illustrations or photographs of prior users that demonstrate before-and-after images simulating before tooth whitening and after tooth whitening. Additionally, some tooth-whitening systems include a strip of material having a spectrum of color variations that simulate the possible spectrum of colors of a consumer's teeth. The strip is held next to a consumer's teeth before, during and after the whitening process to measure the change in color during the whitening process. However, none of these simulate tooth whitening on a consumer's own teeth.

As such, there exists a need to provide products that simulate a change in appearance in color of a consumer's own teeth. Further, there exists a need to provide products that demonstrate the unattractive appearance of stained teeth and the attractive appearance of whitened teeth. Still further, there exists a need for products that simulate a viewer's teeth before, during and after whitening. Yet further, there exists a need to provide products that promote and encourage the use and full compliance of tooth-whitening programs, despite time and cost. Also, there exists a need to provide products that allow a user to compare various gradations of tooth whitening in a single image.

SUMMARY OF THE INVENTION

A reflective device is provided. The reflective device includes a reflective layer and a first region which reflects light to form an image that simulates a change in tooth color of at least a portion of a viewer's tooth.

BRIEF DESCRIPTION OF THE DRAWINGS

While the specification concludes with claims particularly pointing out and distinctly claiming the invention, it is believed that the present invention will be better understood from the following description taken in conjunction with the accompanying drawings in which:

DETAILED DESCRIPTION OF THE PREFERRED EMBODIMENTS

Reference will now be made in detail to the present preferred embodiments of the invention, examples of which are illustrated in the accompanying drawings wherein like numerals indicate the same elements throughout the views and wherein elements having the same two last digits (e.g., 20 and 120) or alphabetical suffix (e.g., 24 and 24A) represent similar elements. As discussed more fully hereafter, the present invention is directed to products comprising reflective devices and methods of using the same. The reflective device preferably has at least one region that reflects an image that simulates a change in appearance in color of at least a portion of a viewer's tooth. More preferably, the region of the reflective device changes the amount and/or character of principally yellow and/or blue wavelengths of the incident light, although, as discussed more fully hereafter, other wavelengths may also be changed. Thus, a viewer is able to compare and contrast a predetermined change in tooth color (e.g., whitened or yellow teeth). As used herein, the term "teeth" is also intended to include the singular as well as a portion of a tooth, and the term "tooth" is intended to also include portions of a tooth as well as the plural.

The change in appearance of tooth color can be accomplished by the region by selectively reflecting, scattering, and/or absorbing one or more predetermined wavelengths of light (i.e., wavelengths of the electromagnetic spectrum between about 380 nm and about 770 nm). Monochromatic light, which is light of a single wavelength or a narrow range of wavelengths, is perceived as a pure or spectral color. For example, light having a wavelength of 680 nm is perceived as a spectral red color while light having a wavelength of 410 nm is perceived as a spectral violet color. Light which is a mixture of wavelengths is perceived as a non-spectral color. For instance, light having a mixture of red spectral light having a wavelength of 700 nm and violet spectral light having a wavelength of 400 nm is perceived as a non-spectral purple color.

Figure 1:
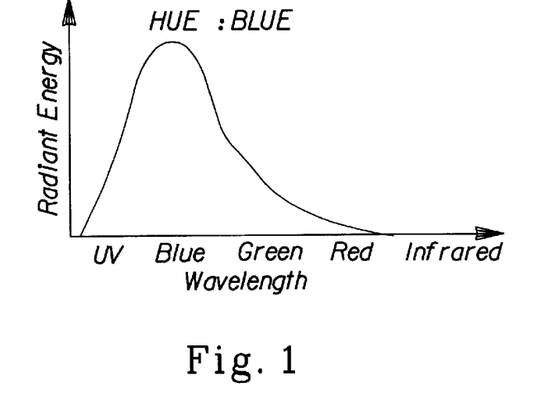
FIG. 1 is a schematic illustration of an exemplary spectral distribution.

While most light is a mixture of wavelengths, light may have a dominant wavelength such that the light is perceived as having a hue and the extent to which the wavelength dominates is known as saturation. For example, light having the spectral distribution illustrated in FIG. 1 would be perceived as having a blue hue. The hue becomes more saturated as the rise and fall or slope of the spectral distribution curve steepens, until a spectral color is reached, which is represented as essentially a vertical line at a particular wavelength.

Figure 2:
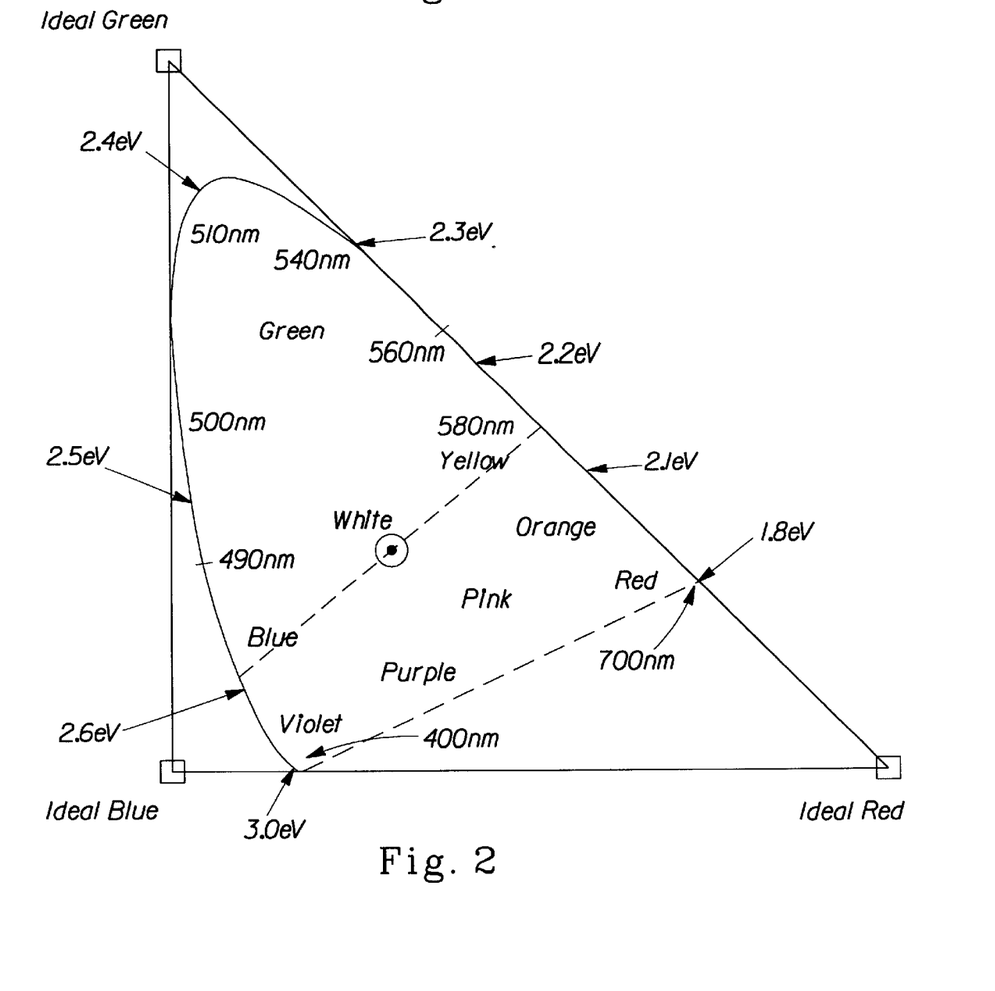
FIG. 2 is a schematic illustration of the 1931 CIE XYZ Chromaticity Diagram.
Figure 3:
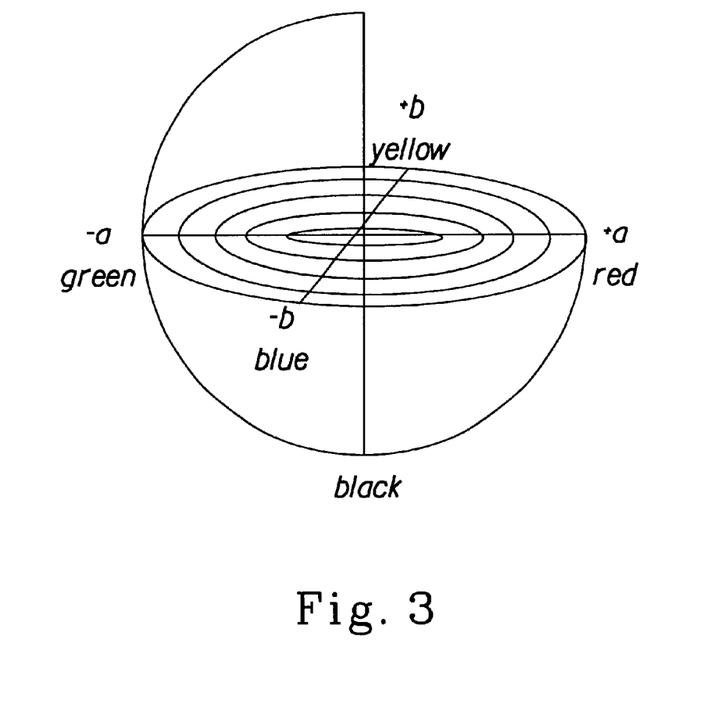
FIG. 3 is a schematic illustration of the 1976 CIE LAB color space.

As shown in FIG. 2, the spectral and non-spectral colors are mapped by the 1931 Commission Internationale de l'Eclairage (CIE) XYZ Chromaticity Diagram, wherein every color is assigned a particular point in the coordinate plane and wherein the solid line represents the spectral colors. However, the CIE XYZ Chromaticity Diagram does not take into account brightness. This was remedied by the 1976 CIE LAB color space, the model of which is shown in FIG. 3. The L value measures brightness and varies from a value of one hundred for perfect white to zero for black. The a* value measures redness when positive, gray when zero and greenness when negative. The b* value measures yellowness when positive, gray when zero and blueness when negative.

Figure 4:
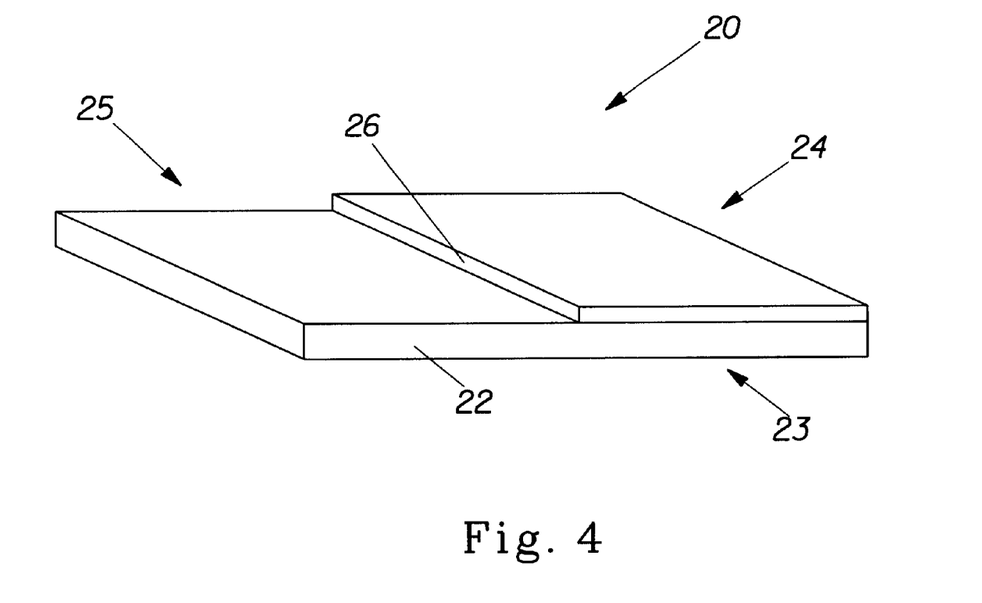
FIG. 4 is a perspective view of a preferred reflective device made in accordance with the present invention.

Referring to FIG. 4, a preferred reflective device in the form of a mirror 20 made in accordance with the present invention will now be described. The mirror 20 comprises a reflective layer 22 which specularly reflects (as opposed to diffuse reflection) some of the light incident thereto so that a tooth image can be perceived. The mirror 20 also has at least one region 24 thereof which is associated with a first portion 23 of the reflective layer 22 and which changes one or more spectral characteristics of light incident thereto to achieve the perceived change in tooth color. Thus, the portion 25 of the reflective layer 22 which is not coextensive with the region 24 merely reflects the incident light substantially unchanged so that the viewer sees his actual (or substantially close to actual) tooth color while the region 24 reflects light having changed spectral characteristic(s) so that the viewer sees a changed tooth color. As used herein, the phrase "spectral characteristic" is intended to refer to any variable whose value quantifies the actual or perceived color composition of light. Thus, spectral characteristics include, but are not limited to, L a* b* values, spectral curve values (e.g., wavelength and percent reflectance), and mathematical manipulations thereof such as sums, differences, products, ratios, etc. The reflective layer 22 can be provided in the form of a glass plate having a silvered surface, a chromed surface, a metallic foil, a metallized polymer film, or in any other form which is capable of providing the desired reflective properties for perceiving a tooth image.

Spectral characteristics of light incident to the region 24 are changed in a predetermined manner to form an image that simulates a viewer's teeth before, during and/or after whitening. To reflect an image that simulates a change in appearance in tooth color to whitened, generally the light reflected from the region 24 of the mirror 20 has an L value that increases from the value of the incident light, an a* value that increases or decreases depending upon whether the stained teeth have a green or red tint prior to whitening, and a b* value which decreases when compared to the incident light. While this is the general relationship for simulating a whitened appearance, the b* value might also increase if the magnitude of the increase of the L value is large enough. Conversely, the L value might also decrease if the magnitude of the decrease of the b* value is large enough. Because the color of actual stained teeth varies by the diets of consumers in different geographies, selection whether the a* value increases or decreases can be geography dependent. For instance, stained teeth have a brown or red tint in the United States while stained teeth have a green tint in China. Thus, the region 24 can be configured to appropriately modify the a* value of incident light to account for the desired color of whitened teeth based on the corresponding geography.

While the mirror 20 can be used to simulate the appearance of whitened teeth, it can also be used to simulate the appearance of yellowed teeth to reinforce the magnitude of a whitening improvement to a viewer. To form an image that simulates a change in appearance in color of teeth to stained or yellowed, the light reflected from the region 24 of the mirror 20 has an L value that generally decreases compared to the incident light, an a* value that increases or decreases depending upon whether the stained teeth have a green or red tint prior to whitening, and a b* value which increases when compared to the incident light. While this is the general relationship for simulating a yellowed appearance, the b* value might also decrease if the magnitude of the decrease of the L value is large enough. Conversely, the L value might also increase if the magnitude of the increase of the b* value is large enough. As will be appreciated, the mirror 20 can also be used to simulate other changes in tooth color, such as incremental points in a whitening process by appropriate selection of the L a* b* values of the spectral layer 26.

As indicated above, the region 24 of the mirror 20 preferably reflects light having a more positive b* value (i.e., increased yellow wavelengths and/or decreased blue wavelengths relative to the incident light) to simulate yellowed or stained teeth. As used herein, the phrases "more positive" and "less positive" are intended to refer to directions along the b* axis of the CIE LAB color space. Thus, a more positive b* value is a value which is displaced along the b* axis in the positive direction. Preferably, the light reflected by the region 24 of the mirror 20 is substantially the same as one of the spectral plots of FIG. 5. Alternatively, the reflected light can be characterized according to its L a* b* values in which case the reflected light has an L value between about 20 and about 100, an a* value between about −20 and about 20, and a b* value between about −10 and about 55. More preferably, the L value is between about 25 and about 98, the a* value is between about −15 and about 15, and the b* value is between about −10 and about 35.

Most preferably, the L value is between about 35 and about 95, the a* value is between about −10 and 10, and the b* value is between about −5 and about 35. Still more most preferably, the L value is about 93, the a* value is about 0, and the b* value is about 6.

Thus, the change in L, a* and b* values ("delta") between the incident light (assuming incident light having an L a* b* values of 100, 0, and 0, respectively) and the reflected light for yellowed teeth is between about 0 and about 80 for the delta L value, between about −20 and about 20 for the delta a* value, and between about −55 and about 10 for the delta b* value. More preferably, the delta L value is between about 2 and about 75, the delta a* value is between about −15 and about 15, and the delta b* value is between about −35 and about 10. Most preferably, the delta L value is between about 5 and about 65, the delta a* value is between about −10 and about 10, and the delta b* value is between about −35 and about 5. Still more most preferably, the delta L value is about 7, the delta a* value is about 0, and the delta b* value is about −6.

Alternatively, the region 24 of the mirror 20 preferably reflects light having a less positive b* value (i.e., decreased yellow wavelengths and/or increased blue wavelengths relative to the incident light) to simulate whitened teeth. More preferably, the light reflected by the region 24 of the mirror 20 is substantially the same as one of the spectral plots of FIG. 6. Alternatively, the reflected light can be characterized according to its L a* b* values in which case the reflected light has an L value in the range between about 20 and about 100, an a* value in the range between about −20 and about 20, and a b* value in the range of between about −10 and about 55. More preferably, the L value is between about 60 and about 90, the a* value is between about −15 and about 15, and the b* value is between about 0 and about 35. Most preferably, the L value is between about 65 and about 85, the a* value is between about −10 and about 10, and the b* value is between about 5 and about 25. Still more most preferably, the L value is about 92, the a* value is about −0.5, and the b* value is about 3.

Thus, the change in L, a* and b* values ("delta") between the incident light (assuming incident light having an L a* b* values of 100, 0, and 0, respectively) and the reflected light for whitened teeth is between about 0 and about 80 for the delta L value, between about −20 and about 20 for the delta a* value, and between about −55 and about 10 for the delta b* value. More preferably, the delta L value is between about 10 and about 40, the delta a* value is between about −15 and about 15, and the delta b* is between about −35 and about 0. Most preferably, the delta L value is between about 15 and about 35, the delta a* value is between about −10 and about 10, and the delta b* value is between about −25 and about −5. Still more most preferably, the delta L value is about 8, the delta a* value is about 0.5, and the delta b* value is about −3.

Spectral characteristic values described herein, unless stated otherwise, are measured using a spectrophotometer known in the art in accordance with ASTM 308. More preferably, the spectrophotometer is a Microflash MF 200 manufactured by Datacolor International of Lawrenceville, N.J., or a similar spectrophotometer. The Microflash MF 200 is a dual beam spectrometer having a measuring geometry which is diffuse illumination/8 degree in accordance with CIE Publication No 15.2 Colorimetry. The spectral range is 400 to 700 nm with a resolution of 3 nr and a measuring range of 0 to 200% reflectance. A D65(CIE) pulsed xenon illuminant and an LAV (Large Angle View) probe are used. The LAV probe is a 66 mm sphere having a measured area of 18 mm and an illuminated area of 22 mm.

Figure 5:
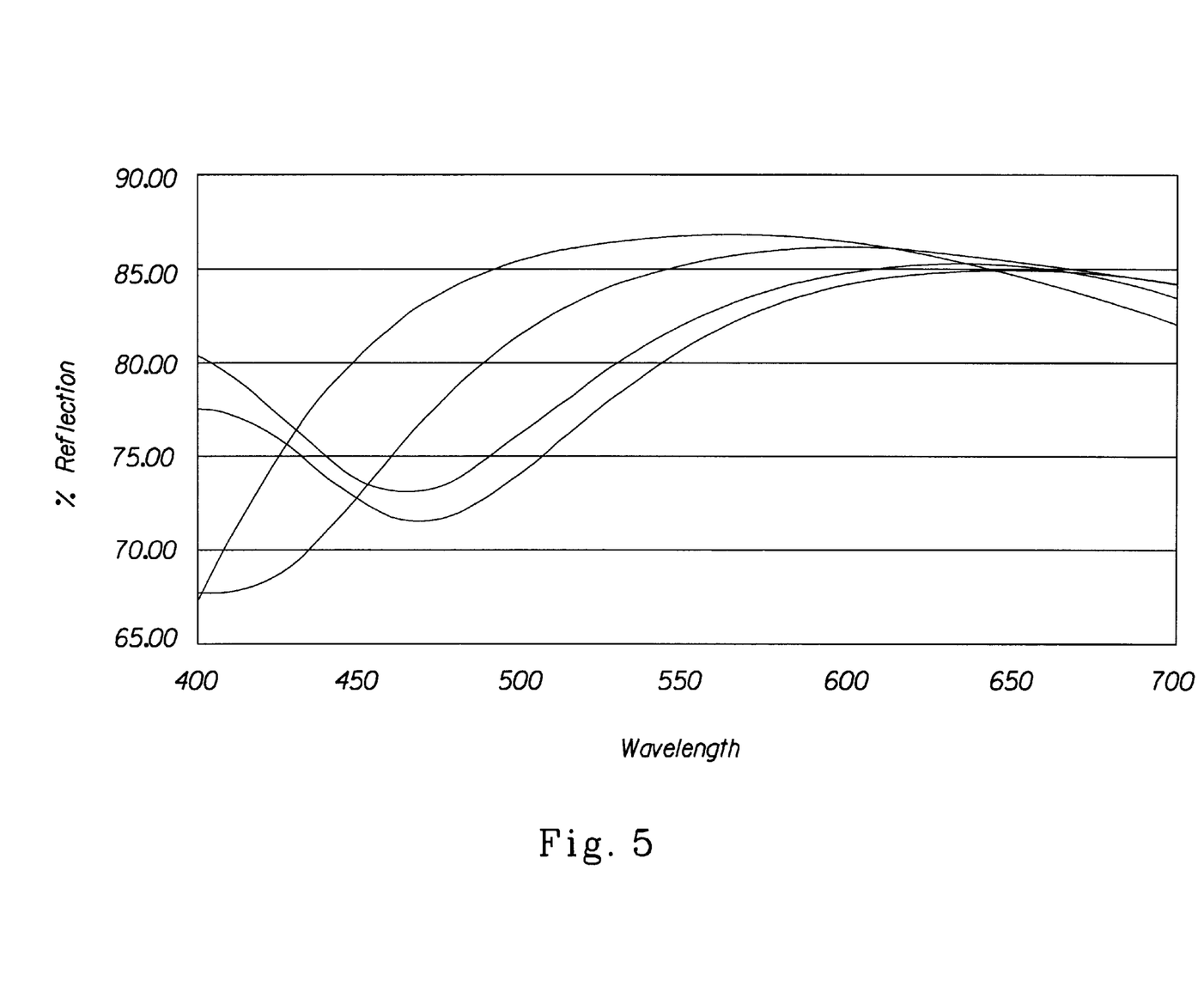
FIG. 5 is a perspective view of another preferred reflective device made in accordance with the present invention.
Figure 6:
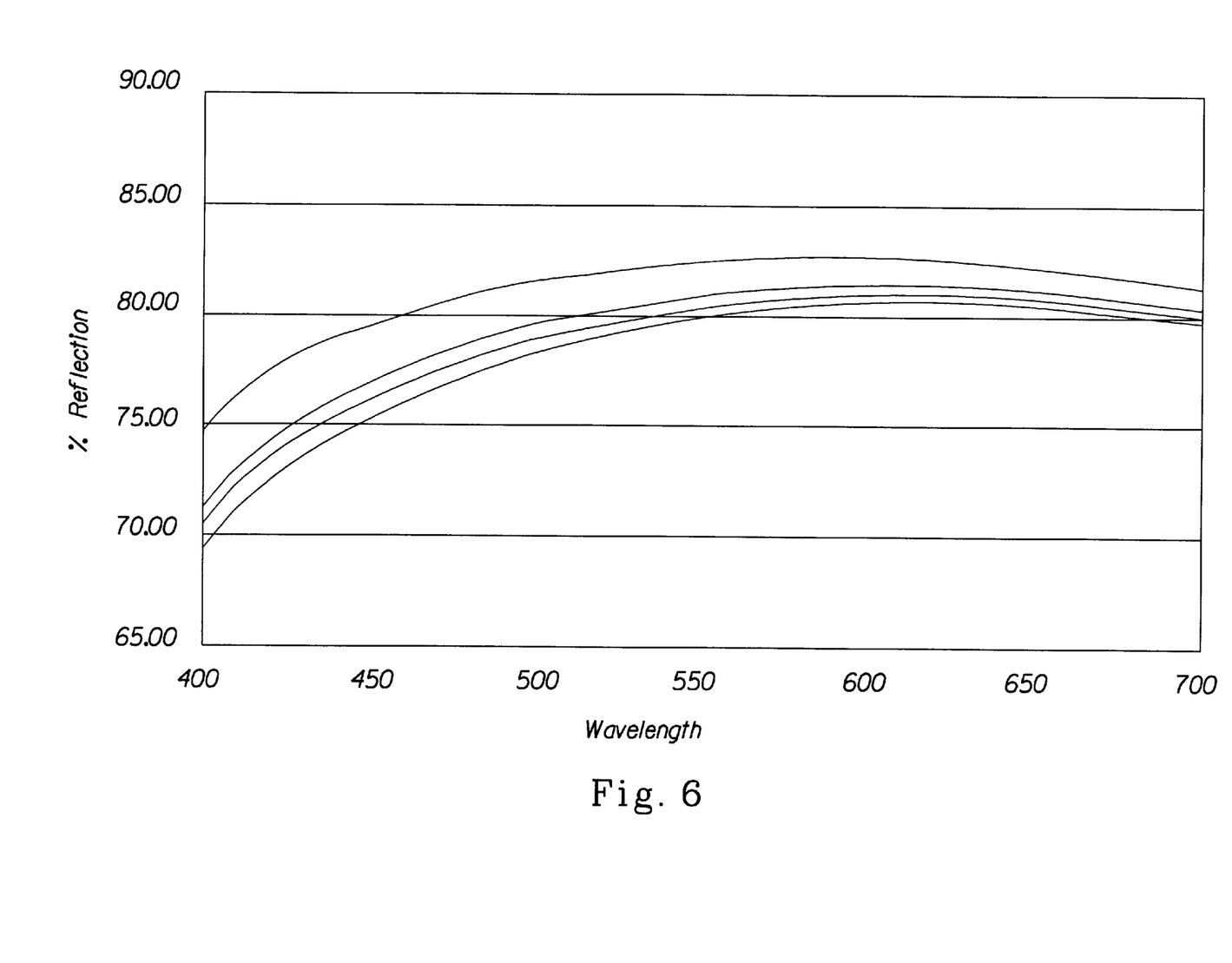
FIG. 6 are spectral plots from a region of a mirror made in accordance with the present invention which simulates yellow or stained teeth.

The region 24 preferably comprises a spectral layer 26 which is adjacent to the reflective layer 22. The spectral layer 26 changes the spectral characteristics of light incident to the region 24 of the mirror so that a change in tooth color is perceived. The spectral layer 26 can be provided in the form of a coating, film, or other layer which is adjacent to the reflective layer 22, wherein the film or coating allows selective transmission of light to the reflective layer 22 adjacent the spectral layer 26. More preferably, the spectral layer 26 is provided in the form of a filter. To provide reflected light with increased yellow wavelengths and/or decreased blue wavelengths (i.e., a more positive b* value) relative to the incident light, a filter such ND 0.10 manufactured by the Eastman Kodak Company of Rochester, N.Y. can be used. The spectral plots for exemplary filters suitable for increasing yellow wavelengths and/or decreasing blue wavelengths are shown in FIG. 5. To provide reflected light with increased blue wavelengths and/or decreased blue wavelengths (i.e., a less positive b* value) relative to the incident light, a filter such as CC05B of the Eastman Kodak Company can be used. The spectral plots for exemplary filters suitable for increasing blue wavelengths and/or decreasing blue wavelengths are shown in FIG. 6. The spectral curves of FIGS. 5 and 6 preferably have a maxima (i.e., a point of inflection) at a wavelength greater than about 500 nm. More preferably, the area under the spectral curves, at wavelengths less than about 550 nm, is greater for the spectral curves of FIG. 6 than the spectral curves of FIG. 5. While the present invention is described herein as comprising a region 24 with a spectral layer which is adjacent to the reflective layer, it will be appreciated that spectral layer 26 may be formed integral with the reflective layer 22 to modify the spectral characteristics of the incident light to form a tooth image having a color change. Alternatively, the spectral layer can be dispersed within the reflective layer (e.g., part of the glass or silvered surface), thereby eliminating the need for a separate and distinct spectral layer 26. The spectral layer can be permanently or removably attached to the reflective layer 22 by means known in the art, such as adhesives or other chemical or mechanical fasteners. Further, one or more of the regions can be provided on one and/or both sides of the reflective device 20. As will be appreciated from the foregoing, region 24 can be structurally and/or functionally associated with the portion 23 of the reflective layer in numerous ways to achieve both reflection and change in the spectral characteristics of the incident light so that a change in tooth color can be perceived.

Figure 7:
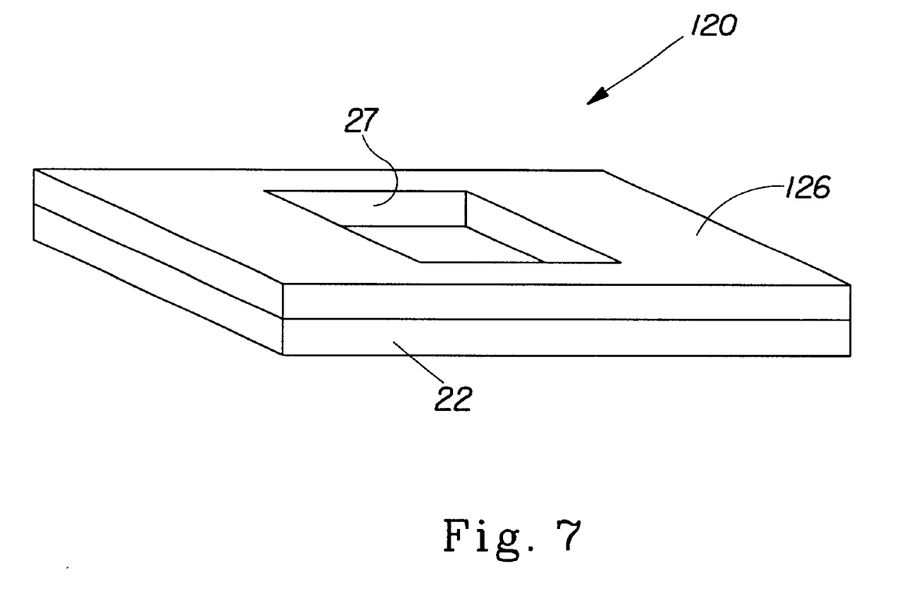
FIG. 7 are spectral plots from a region of a mirror made in accordance with the present invention which simulates whitened teeth.

The reflective devices of the present invention can be provided in a variety of shapes and sizes. Preferably, the mirror is sized to be held conveniently by one or two hands and is capable of reflecting a full image of a viewer's mouth. More preferably, the mirror has a length less than about 20 cm and a width less than about 20 cm. Most preferably, the mirror has a length between about 4 cm and about 12 cm and a width between about 4 cm and about 12 cm. The mirror can be substantially rectangular in plan view or can be provided in the shape of a viewer's mouth or teeth. Alternatively, the reflective device can further include a housing having a mouth-shaped cut out corresponding to the shape of a viewer's mouth or teeth and through which the mirror is visible. Likewise, the region 24 can be provided in a variety of geometric shapes. For example, the region 24 can be square (see, e.g., FIG. 4), rectangular, circular, or combinations thereof in plan view. Alternatively, the region 24 can have a section removed to form a window 27 which exposes the reflective layer (or another spectral layer), as shown in FIG. 7 for the mirror 120. The region 24 preferably has a length less than about 20 cm and a width less than about 20 cm. More preferably, the region 24 has a length less than about 10 cm and a width less than about 10 cm. Most preferably, the region 24 has a length less than about 2 cm and width less about 2 cm to correspond to one or two teeth.

Figure 8:
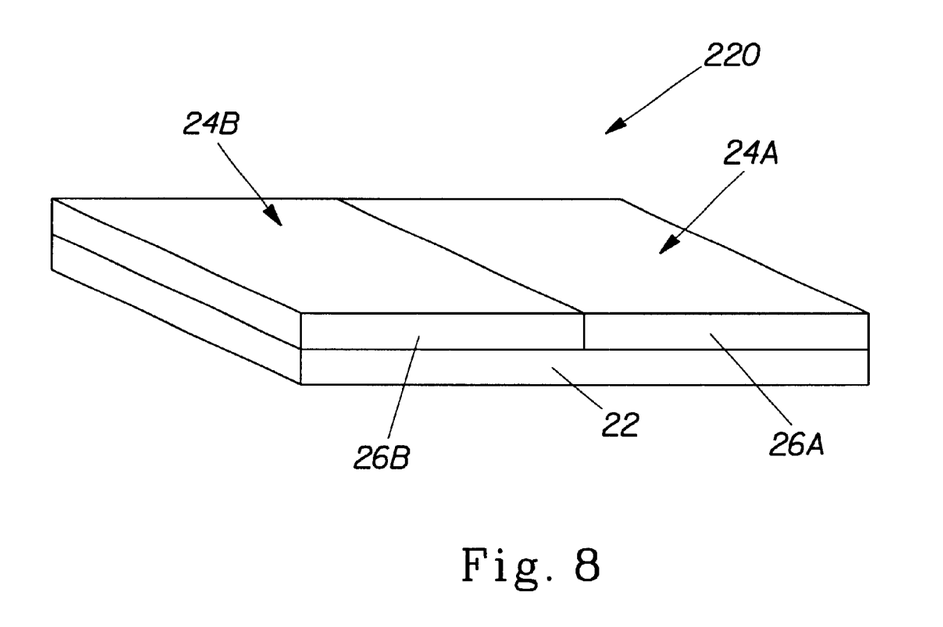
FIG. 8 is a perspective view of yet another preferred reflective device made in accordance with the present invention.

Referring to FIG. 8, another preferred embodiment of the present invention is illustrated in the form of a mirror 220 having a first region 24A and a second region 24B, wherein the first region 24A reflects light having a more positive b* value than the incident light to simulate yellow or stained teeth and the second region 24B reflects light having a more negative b* value than the incident light to simulate whitened teeth. The spectral characteristics of the regions 24A and 24B can be provided as previously discussed with respect to the mirror 20. This arrangement is more useful to more dramatically illustrate a change in tooth color. Like the first region 24A, the second region 24B preferably comprises a spectral layer 26B which can be provided in the form of a filter. Alternatively, the same utility can be achieved with the mirror 20, wherein a plurality of removable filters are used with the mirror 20. For instance, one filter might provide reflected light having a more positive b* value than another filter. Thus, a user can change the filter forming the spectral layer to allow active modification of the light reflected by the region 24 and thereby adjust the image produced by the mirror to his or her preference.

The change in L, a* and b* values ("delta") between the reflected light of region 24A and the reflected light of region 24B is between about −80 and about 80 for the delta L value, between about −40 and about 40 for the delta a* value, and between about −65 and about 65 for the delta b* value. More preferably, the delta L value is between about −38 and about 65, the delta a* value is between about −30 and about 30 and the delta b* value is between about −35 and about 45. Most preferably, the delta L value is between about −30 and about 50, the delta a* value is between about −20 and about 20, and the delta b* value is between about −30 and about −30. Still more most preferably, the delta L value is about 1, the delta a* value is about 0.5, and the delta b* value is about −2.7.

The reflective devices of the present invention may further contain any number of regions for simulating the color of teeth at any point in the whitening process. For example with reference to FIG. 9, the mirror 320 comprises a first region 24A, a second region 24C, a third region 24D, a fourth region 24B, and a portion 25 of the mirror 320 which merely comprises the reflective layer which reflects an unmodified image of the viewer's teeth. The first region 24A reflects a light having a less positive b* value to simulate whitened teeth after a whitening regimen has been completed while the fourth region 24B reflects light having a more positive b* value to simulate yellowed teeth prior to whitening. The second and third regions 24C and 24D might reflect light having b* values between the first and fourth regions 24A and 24B to simulate teeth after one third and two thirds, respectively, of the whitening regimen has been completed. As will be appreciated, any number of regions can be provided and arranged as desired to simulate any number of portions of a whitening regimen for convenience. Thus, the number of regions might correspond to each week of a whitening regimen. Further, these regions can be appropriately sized so that each contributes to part of the image of a viewer's visible maxillary dentition and/or mandibular dentition, as previously discussed, for convenient comparison between tooth color changes.

Figure 9:
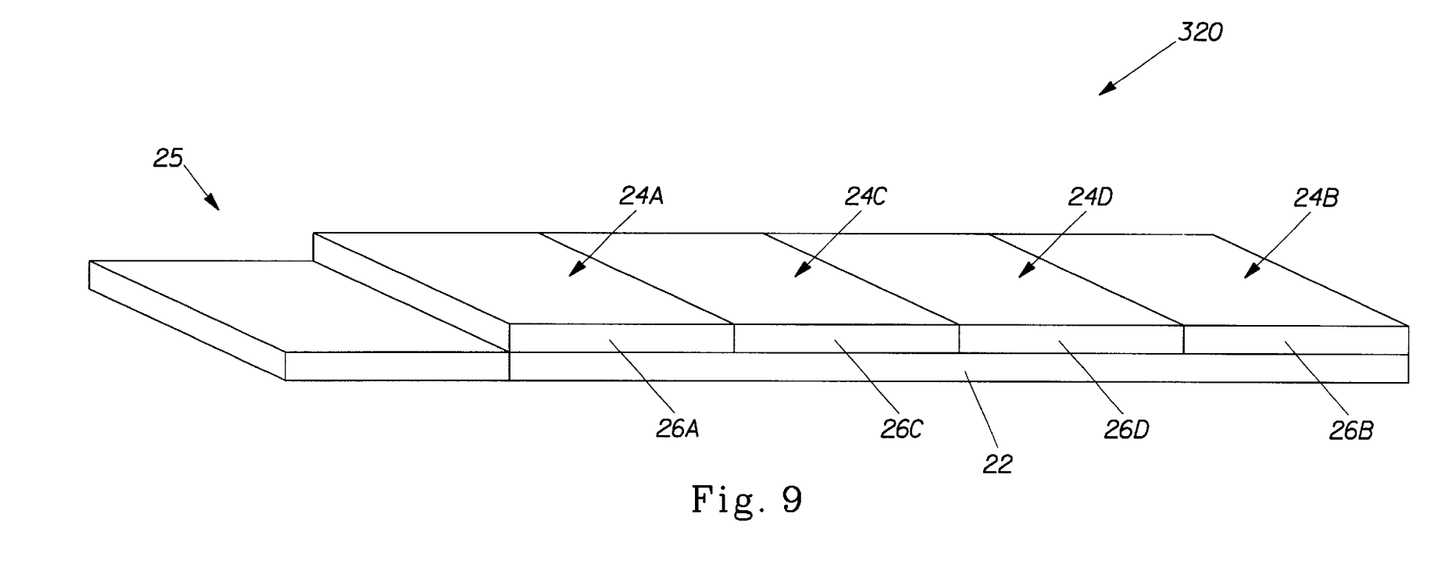
FIG. 9 is a perspective view of still another preferred reflective device made in accordance with the present invention.
Figure 10:
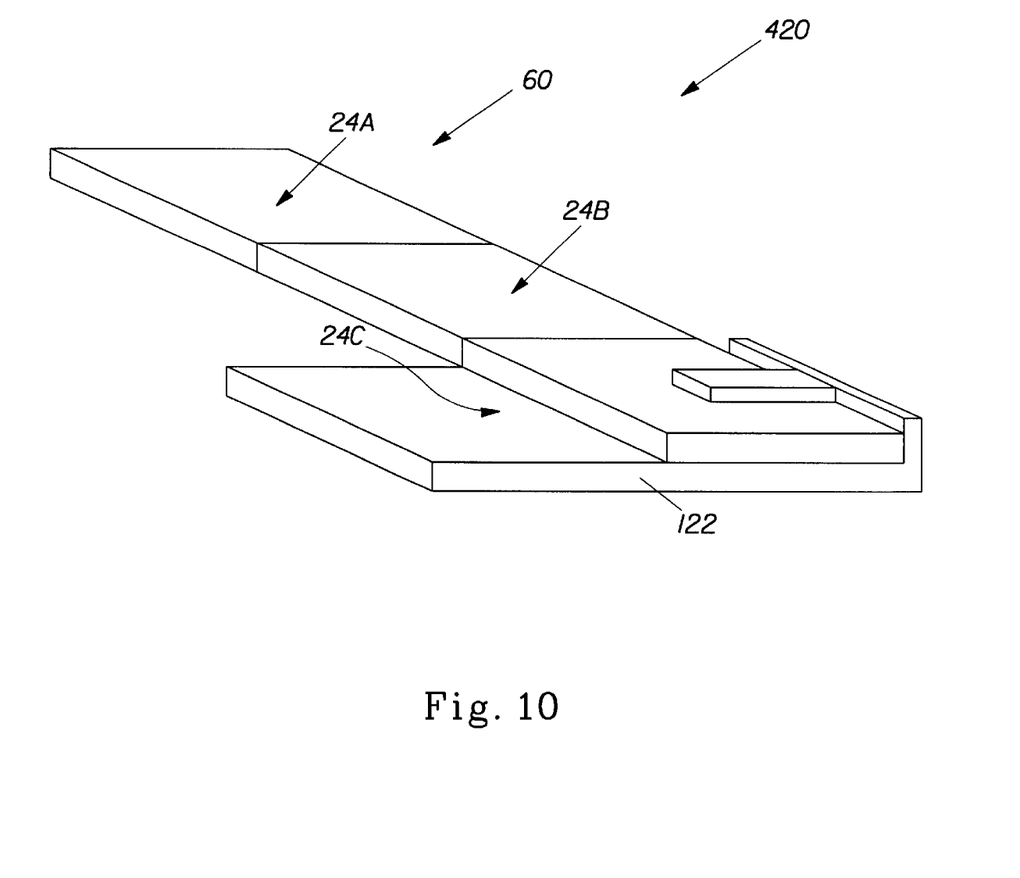
FIG. 10 is yet still another preferred reflective device made in accordance with the present invention.

Referring to FIG. 9, another preferred mirror 420 made in accordance with the present invention is illustrated. The mirror 420 comprises a reflective layer 122 and movable member in the form of a slide 60 which comprises a plurality of regions (e.g., 24A, 24B, and 24C) which change the spectral characteristics of the light incident thereto. A portion of the reflective layer 122 is positioned below the slide 60 so that light is reflected through the region overlying the reflective layer (e.g., 24C), thereby reflecting light to simulate a change in tooth color. Different regions can be moved into position over the reflective layer by merely translating the slide 60. While the movable member is described herein as a slide, it will be appreciated that other movable members might be provided, such as a rotatable wheel which comprises the regions 24A to 24C. The rotatable wheel is rotated to place at least one region in registration with a portion of the reflective layer 122.

Figure 11:
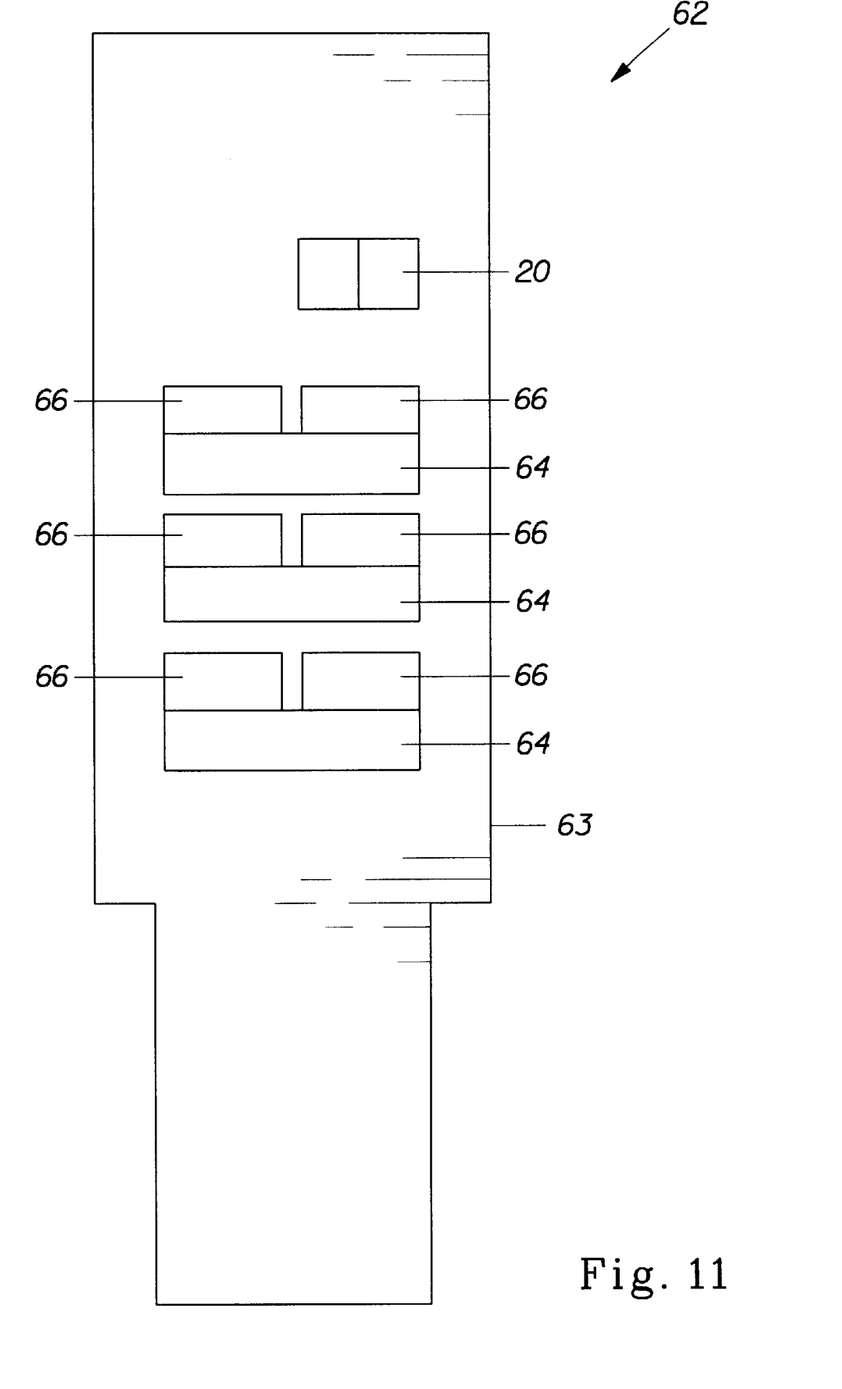
FIG. 11 is a front elevational view of an exemplary display device made in accordance with the present invention.
Figure 12:
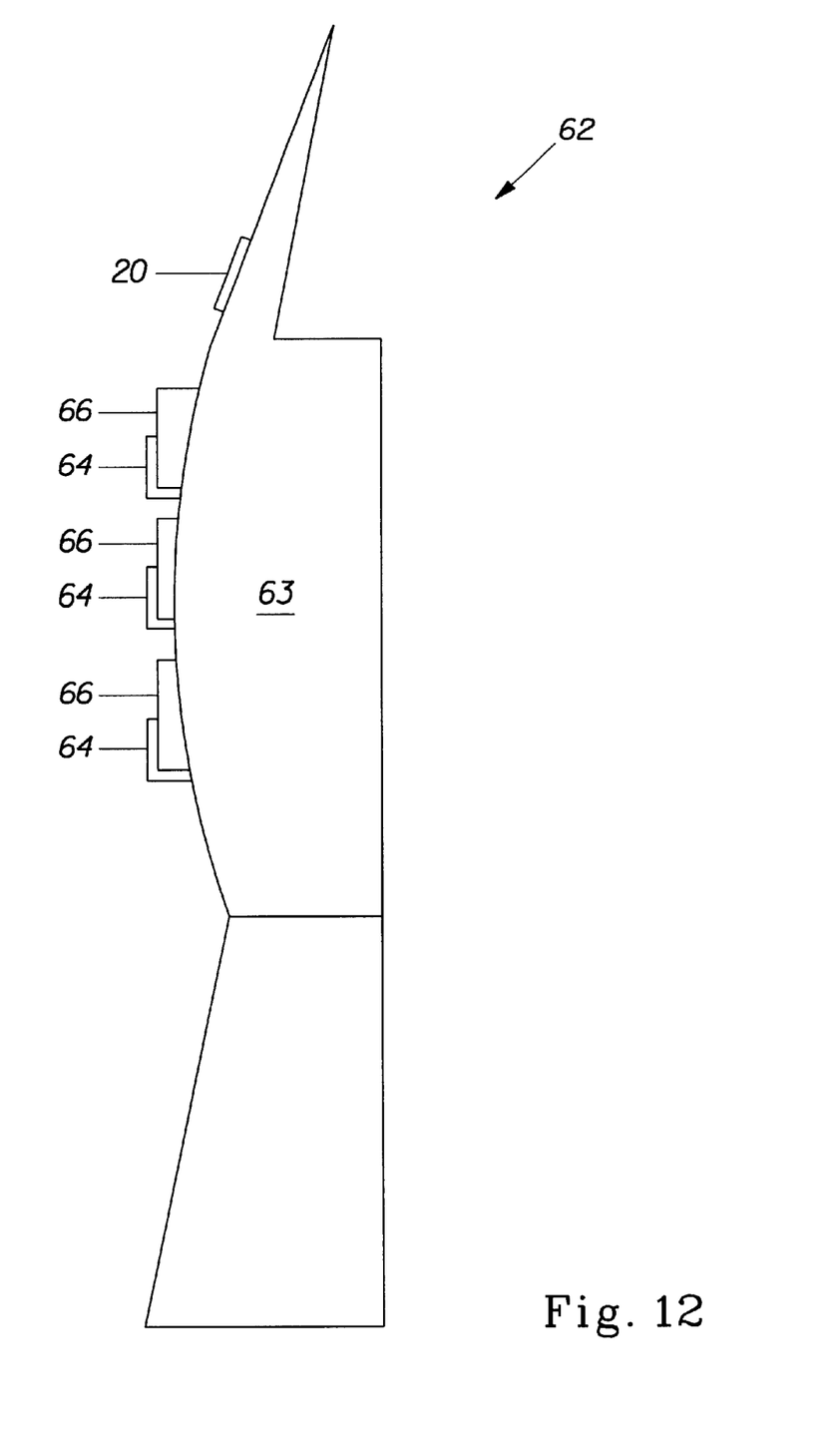
FIG. 12 is a side elevational view of the display device of FIG. 11.

Referring to FIGS. 11 and 12, the reflective devices of the present invention can be incorporated into a display device 62, such as a kiosk, a booth, a shelf fixture, an easel card, or a mini wing display. The mirror can be fixedly (e.g., attached by mechanical or chemical fasteners known in the art), movably (e.g., by translation, rotation, or combinations thereof), or removably associated with a frame 63, stand, or other support structure of the display device 62 to allow convenient viewing by passing consumers within a mall or store. The display device might also contain shelving 64 for storing a plurality of packaged teeth whitening kits 66 (or portions thereof) for sale. One such tooth whitening system is described in U.S. Pat. No. 5,891,453 entitled Delivery System For A Tooth Whitener Using A Strip Having Low Flexural Stiffness, the substance of which is fully incorporated herein by reference. While this is a preferred tooth whitening system for use with the present invention, other tooth whitening systems can also be used. For instance, other tooth whitening compositions and/or delivery systems (e.g., trays, syringes, mouth guards) might be employed as part of the tooth whitening system. A reflective device according to the present invention may also be disposed with the above-described tooth-whitening kits apart from the display device 62.

While the reflective devices have been described herein as comprising a reflective layer and a spectral layer, another preferred embodiment of the present invention comprises a reflective layer and a light source which replaces part or all of the function of the spectral layer, wherein the light source emits a light having the previously described L a* b* values or where the light source in combination with a reflective device provides those L a* b* values. The light source would be positioned close enough to a viewer to illuminate the easily visible maxillary and/or the mandibular dentitions so that an image is reflected from the mirror which simulates the color of the viewer's teeth before, during, or after whitening. The light source could be incorporated into the display device 62 or the light source might be provided with the mirror as a separate kit, optionally in combination with one of the previously described tooth whitening systems. The light source might contain a plurality of interchangeable spectral layers in the form of filters for providing illumination having the L a* b* values for simulating change in teeth color. Alternatively, multiple light sources (e.g., multiple light bulbs having different emission characteristics) might be provided. Thus, numerous means (e.g., integral and/or dispersed spectral layers, light sources, filters, coatings, etc.) have been described herein which can cooperate with the reflective layer of the devices of the present invention to simulate a change in tooth color.

While particular embodiments of the present invention have been illustrated and described, it will be obvious to those skilled in the art that various changes and modifications may be made without departing from the spirit and scope of the invention, and it is intended to cover in the appended claims all such modifications that are within the scope of the invention.

What is claimed is:

1. A method simulating a change in tooth color, comprising:

providing a reflective device comprising a reflective layer, a first region associated with a portion of said reflective layer which changes one or more spectral characteristics of light incident thereto to simulate a first change in tooth color, and a second region associated with another portion of said reflective layer which changes one or more spectral characteristics of light incident thereto to simulate a second change in tooth color; and reflecting light from either of said first or said second regions.

2. The method of claim 1, wherein said first region reflects light having a spectral curve substantially similar to one of the curves of FIG. 5.

3. The method of claim 1, wherein said second region reflects light having a spectral curve substantially similar to one of the curves of FIG. 6.

4. The method of claim 1, wherein the delta L value between incident light and reflected light of said first region is between about 0 and about 80.

5. The method of claim 4, wherein the delta a* value between incident light and reflected light of said first region is between about −20 and about 20.

6. The method of claim 5, wherein the delta b* value between incident light and reflected light of said first region is between about −55 and about 10.

7. The method of claim 1, further comprising at least one additional region distinct from said first and second regions, wherein said at least one additional region reflects light having L a* b* values in between the L a* b* values of said first and second regions.

8. The method of claim 1, wherein said first region further comprises a spectral layer.

9. The method of claim 8, wherein said spectral layer is a filter.

10. The method of claim 9, wherein said filter is removable.

11. The method of claim 8, wherein said spectral layer is a coating.

12. The method of claim 1, wherein said first region is movable.

13. The method of claim 12, wherein said first region translates.

14. The method of claim 1, wherein said reflective device is incorporated in a display device.

15. The method of claim 14, wherein said display device is a kiosk.

16. The method of claim 14, wherein said display device is a shelf fixture.

17. The method of claim 14, wherein said display device further comprises shelving for storing a plurality of tooth whitening systems.

18. The method of claim 1, wherein said first and second regions are adjacent.

19. The method of claim 18, wherein said first region is movable.

20. The method of claim 18, wherein said first region translates.

21. A method simulating a change in tooth color, comprising:

viewing a first tooth image from light reflected from a first region of a reflective device of a display device, wherein said reflective device comprises a reflective layer, said first region associated with a portion of said reflective layer which changes one or more spectral characteristics of light incident thereto to produce said first tooth image to simulate a first change in tooth color, and a second region associated with another portion of said reflective layer;

viewing a second tooth image from light reflected from said second region of said reflective device; and purchasing a tooth whitening system stored with said display device.

22. The method of claim 21, wherein said second region reflects light which is substantially unchanged from the incident light.

23. The method of claim 21, wherein said second region changes one or more spectral characteristics of light incident thereto to simulate said second change in tooth color.

24. The method of claim 21, wherein said first region reflects light having a spectral curve substantially similar to one of the curves of FIG. 5.

25. The method of claim 21, wherein said second region reflects light having a spectral curve substantially similar to one of the curves of FIG. 6.

26. The method of claim 21, wherein the delta L value between incident light and reflected light of said first region is between about 0 and about 80.

27. The method of claim 26, wherein the delta a* value between incident light and reflected light of said first region is between about −20 and about 20.

28. The method of claim 27, wherein the delta b* value between incident light and reflected light of said first region is between about −55 and about 10.

29. The method of claim 21, further comprising at least one additional region distinct from said first and second regions, wherein said at least one additional region reflects light having L a* b* values in between the L a* b* values of said first and second regions.

30. The method of claim 21, wherein said first region further comprises a spectral layer.

31. The method of claim 30, wherein said spectral layer is a filter.

32. The method of claim 31, wherein said filter is removable.

33. The method of claim 30, wherein said spectral layer is a coating.

34. The method of claim 21, wherein said display device is a kiosk.

35. The method of claim 21, wherein said display device is a shelf fixture.

36. A kit, comprising:
a tooth whitening system;
a reflective device;
a means for use with said reflective device which simulates a change in tooth color; and
a package storing said tooth whitening system, said reflective device and said means.

37. The kit of claim 36, wherein said means is a light source having a spectral curve substantially similar to one of the curves of FIG. 5 or 6.

38. The kit of claim 36, wherein said means is a region of said reflective device.

39. The kit of claim 38, wherein said region further comprises a spectral layer.

* * * * *